United States Patent [19]

Restelli et al.

[11] Patent Number: 5,539,087
[45] Date of Patent: Jul. 23, 1996

[54] ANTIBIOTIC A/16686 RECOVERY PROCESS

[75] Inventors: Ermenegildo Restelli, Gerenzano; Luigia Mainoli, Varese, both of Italy

[73] Assignee: Gruppo Lepetit SpA, Gerenzano, Italy

[21] Appl. No.: 444,808

[22] Filed: May 18, 1995

Related U.S. Application Data

[63] Continuation of Ser. No. 341,324, Nov. 16, 1994, abandoned, which is a continuation of Ser. No. 203,889, Mar. 1, 1994, abandoned, which is a continuation of Ser. No. 13,597, Feb. 4, 1993, abandoned, which is a continuation of Ser. No. 860,303, Mar. 27, 1992, abandoned, which is a continuation of Ser. No. 608,426, Nov. 2, 1990, abandoned.

[30] Foreign Application Priority Data

Nov. 7, 1989 [EP] European Pat. Off. .............. 89120577
Dec. 27, 1989 [EP] European Pat. Off. .............. 89123994

[51] Int. Cl.⁶ .............................. C07K 1/14; C07K 1/30; A61K 38/12; C12P 21/04
[52] U.S. Cl. .......... 530/412; 530/300; 530/317; 530/322; 530/344; 530/418; 530/419; 530/421; 435/71.1; 435/71.3
[58] Field of Search ..................... 530/300, 317, 530/322, 344, 412, 418, 419, 421; 435/71.1, 71.3

[56] References Cited

U.S. PATENT DOCUMENTS

| | | | |
|---|---|---|---|
| 4,245,047 | 1/1981 | Higashide et al. | 435/170 |
| 4,298,600 | 11/1981 | Higashide et al. | 435/170 |
| 4,347,322 | 8/1982 | Johnson et al. | 435/179 |
| 4,695,545 | 9/1987 | Nakatsukasa | 435/253.5 |
| 4,713,331 | 12/1987 | Michel et al. | 435/253.5 |
| 5,024,937 | 6/1991 | Penticoff et al. | 435/243 |

FOREIGN PATENT DOCUMENTS 0318680 6/1989 European Pat. Off. .

OTHER PUBLICATIONS

Bardone, et al. "Teichomycins, New Antibiotics from *Actinoplanes Teichomycticus* Nov. Sp." J. Antibiotics 31(3): 170–177 1978.
Cavalleri, et al. "A–16686, A New Antibiotic from Actinoplanes" J. Antibiotics 37(4) 309–317 1984.
Derwent Abstract No. 364736/50.

*Primary Examiner*—Mindy Fleisher
*Assistant Examiner*—Nancy J. Desen
*Attorney, Agent, or Firm*—J. Michael Dixon

[57] ABSTRACT

The present invention is directed to a process for recovering the antibiotics produced by fermentation of Actinoplanes sp. ATCC 33076 or a producing mutant thereof, from a fermentation broth or a process stream, which comprises extraction of the antibiotics by a non-ionic surfactant or a cationic surfactant miscible with or dispersable in water and capable of dissolving the antibiotics, formation of two phases in the first of which the antibiotic and the surfactant are present together, and separation of the antibiotic from the surfactant by addition of suitable organic solvents.

6 Claims, No Drawings

ANTIBIOTIC A/16686 RECOVERY PROCESS

This is a continuation of application Ser. No. 08/341,324, filed Nov. 16, 1994, now abandoned, which is a continuation of application Ser. No. 08/203,889, filed Mar. 1, 1994, now abandoned, which is a continuation of Ser. No. 08/013,597, filed Feb. 4, 1993, now abandoned, which is a continuation of Ser. No. 07/860,303, filed Mar. 27, 1992, now abandoned, which is a continuation of Ser. No. 07/608,426, filed Nov. 2, 1990, now abandoned, herein incorporated by reference.

The present invention relates to a glycolipodepsipeptide antibiotic named antibiotic A/16686 and more specifically to a process for recovering it from a fermentation broth or a process stream containing it.

Antibiotic A/16686 is an antibiotic produced by Actinoplanes sp. ATCC 33076 active against aerobic and anaerobic gram-positive bacteria, including methycillin-resistant Staphylococci and bacteria resistant to ampicillin and erythromicin and it is described in U.S. Pat. No. 4,303,646 together with its manufacture process and pharmaceutical composition containing it.

Preliminary physico-chemical characterization indicated that antibiotic A/16686 is formed by a peptidic core carrying two D-mannose units (Cavalleri et al. J. Antibiotics 37: 309–317, 1984).

It was then found that three closely related components could be isolated from antibiotic A/16686 which were named factor A1, A2 and A3. Factor A2 (ramoplanin) is the component obtained in preponderant amount and is the most relevant for the biological activity, while factor A1 and A3 are obtained in a minor amount. These substances as well as their preparation and uses are described in U.S. Pat. No. 4,427,656.

A method for selectively enhancing the production of factors A2 and/or A3 of antibiotic A/16686 by adding appropriate precursors to an A/16686 producing culture, is described in European Patent Application Publication No. 259780.

Recent studies showed that these three factors have a common cyclic depsipeptide skeleton composed by seventeen aminoacids and a dimannosyl unit. Three different unsaturated fatty acid residues differentiate the three components of the complex.

The antibiotics characterized by the simultaneous presence of a depsipeptide skeleton, fatty acids and sugar moieties have been defined in the scientific literature as glycolipodepsipeptide antibiotics (see Ciabatti et al. Journal Antibiotics 42: 254–267 1989).

The following formula I can be suggested for the three closely related components of antibiotic A/16686:

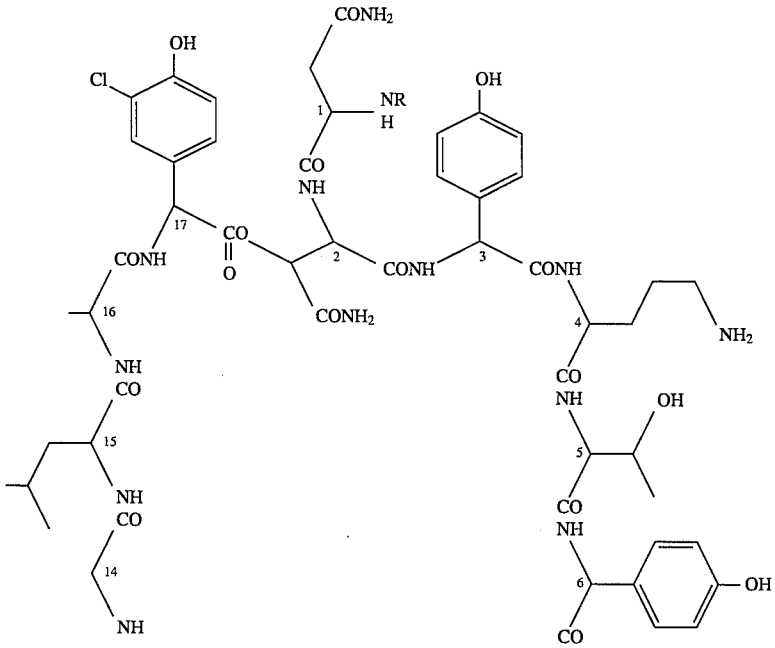

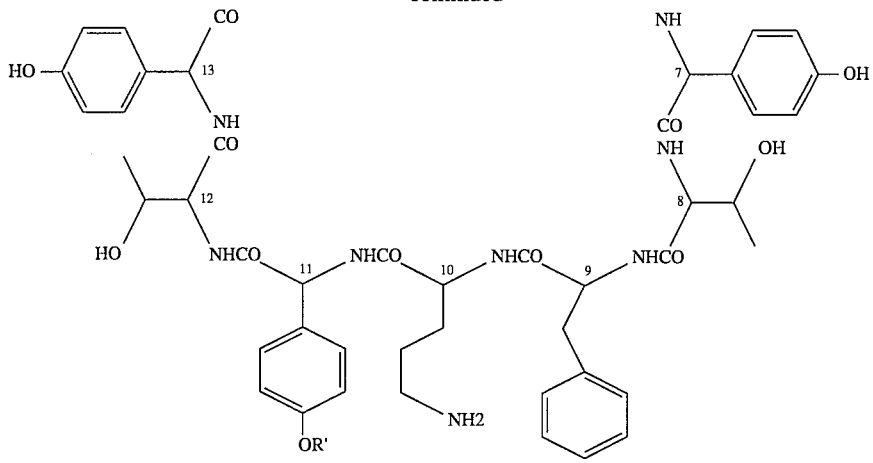

-continued wherein:
R is:
—CO—CH=CH—CH=CH—CH$_2$—CH$_2$—CH$_3$,
—CO—CH=CH—CH=CH—CH$_2$—CH(CH$_3$)$_2$ or
—CO—CH=CH—CH=CH—CH$_2$—CH$_2$—CH(CH$_3$)$_2$
and
R' is a dimannosyl moiety.

European Patent Application Publication No. 318680 describes other compounds related to antibiotic A/16686 complex.

Said compounds, named factors A'1, A'2 and A'3 respectively, are produced by Actinoplanes sp. ATCC 33076 under appropriate conditions and correspond to factors A1, A2 and A3 of formula I wherein R' is a mannosyl moiety.

In general, when recovering an antibiotic from the fermentation broth in which it is produced, it is important to optimize the process in order to obtain a maximum amount of the antibiotic by using a minimum number of steps.

High recovery yields are particularly important when the antibiotic is produced in a large scale for commercial purposes.

In such cases the antibiotic has to be isolated from large amount of a complex fermentation mixture which contains not only the antibiotic but also contains unsoluble mycelium suspended in aqueous solutions of unreacted medium nutrients and other by-products.

The problem of a recovery process is even more complicated if, as in the case of antibiotic A/16686, a large portion of the antibiotic produced by fermentation of the appropriate microbial strain remains trapped in the biomass.

In this case, in order to optimize the recovery yield of the antibiotic, it is necessary to carry out two parallel processes, one on the filtered broth and the other on the mycelial cake.

The process described in U.S. Pat. No. 4,303,646 to recover crude antibiotic A/16686 includes two separate operations the first of which essentially consists in separating the mycelium from the fermentation broth by filtration, extracting the mycelial mass with a mixture methanol/water, isolating the crude fermentation product from this extract, and separating and purifying the antibiotic substances from the isolated crude product. The second one essentially consists in treating the filtered broth with n-butanol, concentrating the organic extract under reduced pressure, adding petroleum ether and separating the resulting precipitate. Two crops of raw material are thus obtained which can be further purified separately or can be combined for this purpose.

The process above described cannot be used to make large quantities of antibiotic A/16686 as those required for its commercial use. In fact, the extremely slow filtration of the biomass makes this operation extremely difficult and potentially unsafe.

Surprisingly, it has been found that it is possible to recover antibiotic A/16686 in high yields by operating directly on the resulting fermentation batch, without separating the filtered broth from the mycelium, or on a process stream by means of a process which comprises contacting the fermentation broth or said process stream with an appropriate amount of a surfactant selected from:
(a) a non-ionic surfactant, or
(b) a cationic surfactant
miscible with or dispersable in water in any proportion and capable of dissolving the antibiotic, then working the mixture in a way that two phases are formed, separating the phase containing the exhausted broth from the surfactant phase and recovering the antibiotic from this latter phase by addition of an organic solvent in which the antibiotics are insoluble.

The advantages of the process of the invention over the above mentioned procedure are essentially:
no handling of large amount of mycelium and no use of large volume of solvent
the possibility to avoid the critical separation from alcohol-water mixtures.

In the art, there are described many cell disintegration techniques both chemical and mechanical which could be used to favor the release of biological products from the biomass: such as for example, the rupture of the membrane by osmotic shock, the digestion of the cell wall by enzymes, the solubilization of cell membrane by anionic, cationic or non-ionic detergents, the lipid dissolution by organic solvents, the saponification by alkali treatment, the ultrasonication and the like, and it is difficult to foresee the most feasible means for recovering an antibiotic substance (Bioseparation, chapter 4, Belter et al. Wiley and Sons, 1988, New York) when most of it is trapped in the biomass of the producing microorganism. Furthermore, these methods refer in a particular way to proteins produced by genetically manipulated bacteria or simple bacteria and there is no suggestion for what concerns the best technique to be used for a substance of more complex nature, such as a glycolipodepsipeptide antibiotic.

In U.S. Pat. No. 4,746,511 is described a lipopolysaccharide, an antitumoral substance formed by a polysaccharide containing D-arabinose and D-mannose coupled with a fatty acid having 14 to 19 carbon atoms through an ester linkage, which is removed from cell body components of Actinomycetes bacteria by a non-ionic surfactant.

According to U.S. Pat. No. 4,746,511 it seems that said substance, which is completely different from antibiotic A/16686, is a cell wall component and therefore the teaching of U.S. Pat. No. 4,746,511 that a non-ionic surfactant may be used in the extraction of some bacterial cell components should discourage a skilled technician to apply similar extraction methods for the recovery of an antibiotic substance trapped in the biomass since, even if said extraction could occur, it would be accompanied by the extraction of cell wall materials, thus bringing further problems of separation from the solubilized components of the cell.

In Czechoslovak Patent No. 231.279 (Chemical Abstracts 216180J Vol. 107, 1987) the antibiotic tylosin (which is a macrolidic antibiotic different from the glicolipodepsipeptide antibiotic of the invention) is separated from the fermentation medium by adding a cationic detergent (trimethyldodecylhexa-decyl ammonium chloride) in the presence of HCHO and $Al_2(SO_4)_3$. The mixture is then extracted by BuOAc precipitated by tartaric acid, dissolved in water, filtered on active carbon and reprecipitated by adding NaCl.

Nothing in the art known to the inventors suggests the use of surfactants for the direct extraction of a glycopeptide antibiotic from its fermentation batch avoiding the use of large amounts of solvents for the isolation of the desired products from organic-water mixtures.

The improved process of the present invention comprises the extraction of the antibiotic A/16686 obtained cultivating the strain ATCC 33076 according to known techniques by contacting the fermentation batch with an appropriate amount of a surfactant selected from:

(a) a non-ionic surfactant, or (b) a cationic surfactant miscible with or dispersable in water, provoking the separation of the mixture in two phases, separating the phase containing the exhausted broth from the surfactant phase and recovering the antibiotic from this latter by addition of an organic solvent.

Any antibiotic or a mixture thereof produced by fermentation of Actinoplanes sp. ATCC 33076 (which strain has been deposited with the permanent culture collection ATCC, 12 Parklawn Dr., Rockville, Md. 20852, U.S.A., as described in U.S. Pat. No. 4,303,646 and is now freely available and accepted under the Budapest Treaty as of Jan. 31, 1981) or a producing mutant thereof (i.e., natural or artificial mutant capable of producing the same substances) can be recovered by applying the process of the present invention, i.e. the antibiotic A/16686 complex, each of the three related factors A1, A2 and A3 described in U.S. Pat. No. 4,303,646, and U.S. Pat. No. 4,427,656 or a mixture thereof in any proportion, the single factors enriched mixtures obtained by adding to the culture the appropriate precursor for enhancing the production of the single factors described in European Patent Application Publication No. 259780 and the antibiotic compounds named A/16686 factors A'1, A'2 and A'3 disclosed in European Patent Application Publication No. 318680.

The process of this invention can be applied to a fermentation broth or to any process stream containing said antibiotics or a mixture thereof.

In the specification and claims the expression "non-ionic surfactant" refers to a surface active substance which bears essentially no charge when dissolved in aqueous media and is based on a water soluble polymer having a hydrophobic portion (e.g. an alkyl benzene moiety) and a hydrophilic one (e.g. a polyoxy-lower alkylene moiety). Accordingly, the expression "cationic surfactant" in the specification and claims means detergents which in aqueous solution form positively charged surface-active ions. When in the specification and claims reference to the general term "surfactant" is made, it comprises both a non-ionic surfactant (a) and a cationic surfactant (b) as defined above.

The surfactant which is used according to the present invention has to be miscible with or dispersable in water. This means that the suitable surfactant forms a clear solution or a stable dispersion with water at a temperature compatible with the usual conditions of industrial recovery process in term of energy consumption, stability of the product, and safety. Generally, for economic reasons which are essential in industrial scale processes, it is preferred to use surfactants which are miscible with water at a temperature comprised between 0° C. and 90° C. although temperatures outside this range are not preclusive of a successful accomplishment of the process of the invention. The most preferred surfactants which are used in the present invention are miscible (or dispersable) with water in any proportion at a temperature comprised between 0° C. and 65° C.

The expression "capable of dissolving the antibiotic" means that the surfactant, must have the capability of retaining in its own phase most of the antibiotic substance. This capability can be preliminary determined by means of tests carried out on samples of the fermentation broth with a series of surfactants and determining the content of antibiotic in the surfactant phase by usual analytical methods for instance by HPLC.

The term "appropriate amount" means that in the extraction step the amount of surfactant added to the fermentation batch must be sufficient to promote the release of the antibiotic substance trapped in the biomass and of course to extract it when the separation in two phases occurs.

Among the non-ionic surfactants (a), are preferred the polyoxyethylene surfactants, e.g. the alkylphenoxypoly(ethyleneoxy)ethanols (ethoxylated alkylphenols).

It is known that the water solubility of polyoxyethylene non-ionic surfactants is dependent on the hydrophilic nature of the ether linkages in the polyoxyethylene chain. These ether linkages are readily hydrated at room temperature and the water solubility of the products at room temperature is dependent on the number of such hydrated ether linkages.

Thus it is possible to define a Hydrophilic-Lipophile-Balance (HLB) the values of which ranges from 0 (completely lipophilic or oil loving) to 20 (completely hydrophilic or water loving). The HLB value is calculated through the following equation:

$$HLB = -(v-45.7)/2.36$$

wherein $v$ is the interfacial tension (see Journal of Pharmaceutical Sciences, Vol 50, No. 9, September 1961, pages 732–736).

For practical purposes it can be approximately calculated by dividing the weight percent of ethylene oxide in the surfactant mole by 5.

Generally, the suitable polyoxyethylene surfactants used according to the present invention have a HLB value of at least 10.

In particular, are preferred those ethoxylated alkyl phenols wherein the alkyl group is a $C_8$–$C_9$ alkyl, preferably octyl, iso-octyl, t-octyl and nonyl, and the number of ethylene oxide units ranges from 6 to 30, preferably from 7 to 13.

In a preferred embodiment of the invention, the non-ionic surfactant is a polyoxyethylene tert-octylphenyl ether containing 7–10 ethyleneoxide units per mole of hydrophobe, such as those commercially known as Triton® X-100 and Triton® X-114 (Rohm & Haas).

Among the non-ionic surfactants can be also conveniently used the ethoxylated anhydrosorbitol esters surfactants, for example those ethoxylated sorbitan fatty acid esters surfactants wherein the sorbitan ester is the monooleate.

For instance a polyoxyethylene derivative of sorbitan monooleate containing 20 oxyethylene units per mole of ester may be employed as non-ionic water miscible surfactant in the process of this invention.

Among the cationic surfactants (b), amine oxides and polyoxyethylene amines are preferred. Amine oxides are particularly preferred.

Amine oxides are well known cationic surfactants which can be also considered as non-ionic compounds having a strong dipolar nitrogen-oxygen bond which exhibits either a non-ionic or cationic character in aqueous solutions depending upon the pH. At pH 3 the cationic form predominates while at higher values of pH (for instance from neutral values on) the non-ionic form predominates.

Examples of suitable amine oxides which can be conveniently used in this invention are those having general formula I

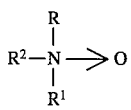

I wherein $R^1$ and R each independently represents a $(C_1–C_4)$alkyl, preferably methyl, or a $(C_1–C_4)$ hydroxy alkyl, preferably hydroxy ethyl, and $R^2$ is an alkyl chain having from 10 to 25 carbon atoms optionally containing amide groups.

More preferably, the amine oxides used in the process of the invention are alkyldimethylamine oxides of formula:

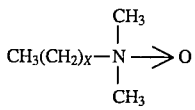

wherein X is from 11 to 17 such as for example lauryl dimethylamine oxide, commercially known as Ammonyx® LO (ONYX Chem. CO.) or alkyl amido propyl dimethylamine oxides of formula:

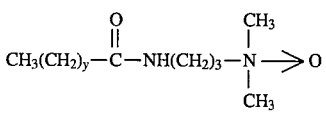

wherein y is an integer from 6 to 16 such as, for example, in the commercial products known as Ammonyx® CDO or TDO (ONYX Chem. Co.) wherein the acyl portion is derived from fatty acids mixtures resulting from hydrolysis of coconut oil and tallow oil, respectively.

Other preferred cationic surfactants are polyoxyethylene amines. In particular polyoxyethylene linear alkyl amines or polyoxyethylene aliphatic t-alkyl amines may be used.

The ethoxylated amines have the characteristic to increase the water solubility as the polyoxyethylene content increases.

Also for these cationic surfactants (b) it is possible to define the Hydrophilic-Lipophilic-Balance (BLB) equation defined above and, generally, the suitable cationic surfactants used according to the present invention have a HLB value not higher than 19.4 and preferably comprised between 14 and 18.

Under the usual conditions of the process the concentration of the non-ionic surfactants (a) can range from 2% to 10% v/v with respect to the fermented broth, preferably from 3% to 6% v/v, while for the cationic surfactants (b), the concentration can range from 0.5% to 10% v/v with respect to the fermented broth, preferably from 1% to 7% v/v.

It is advisable to carry out the extraction at a temperature which is close to room temperature or somewhat lower e.g. from 0° C. to 30° C. avoiding to use operating temperatures higher than 30° C.–40° C. which can provoke the thermal degradation of the broth.

Moreover, it is preferred to carry out the extraction in an acidic medium, more preferably the pH of the fermentation batch is adjusted at a value ranging between 1 and 3. In fact, when a higher pH is applied, the extraction may be incomplete with the same concentration of the surfactant.

In general, after addition of the appropriate amount of surfactant, the mixture is maintained for 30–60 minutes under stirring which period of time is largely sufficient to have the complete extraction of the antibiotic substance.

After the extraction is completed, it may be useful to filter the mixture in order to eliminate the residual wet mycelium. Accordingly, an aqueous solution (or dispersion) is obtained which contains the surfactant and most of the antibiotic produced through the fermentation process.

The filtration is performed according to known techniques using a filter aid such as a diatomaceous earth filter (for instance a Clarcel Flo-Ma) for example according to the already cited U.S. Pat. No. 4,303,646.

A critical aspect of the present invention concerns the removal of the antibiotic from the aqueous mixture containing the surfactant. This is an important problem to solve since both antibiotic A/16686 and the surfactant are soluble or dispersable in water.

Absorption onto resins proved to be not selective.

Addition of large amounts of a non-solvent could permit to precipitate the antibiotic but this operation is hardly feasible in an industrial scale process both for economical and safety reasons.

It has been found that a satisfactory solution of the problem consists in modifying the physico-chemical conditions of the aqueous mixture to provoke its separation in two phases one of which contains most of the antibiotic originally present in the fermentation broth. This phase is subsequently worked out to recover the desired antibiotic. The modification of the physico-chemical conditions which provoke the separation of the mixture in two phases can be accomplished for instance by increasing the temperature. An increase of the temperature, reduces the forces of hydration and the surface active agent become less soluble in the aqueous mixture and then the mixture separates into an organic layer and an aqueous layer.

According to this invention, a substantial amount of the antibiotic is retained by the surfactant phase and the aqueous layer may be eliminated.

Of course, to avoid thermal degradation of the antibiotic during the separation step, it is preferred to raise the temperature only to a limited value. Usually, where the extraction step is carried out at room temperature, the increase of the temperature for phase separation which does not affect the stability of the antibiotic is of 15° C.–30° C. above the room temperature. If the extraction step is carried out at a temperature lower than the room temperature, the temperature increase for provoking the separation into two layers may be of the order of 30° C.–55° C.

In order not to increase the temperature too much, the addition of electrolytes to the water-surfactant mixture resulting from the extraction may be an useful method to favor the separation in two phases of said mixture.

As for the non-ionic surfactants, they are normally characterized by a "cloud point", which is the temperature above which all but very dilute aqueous solutions form two phases. The effect of dissolved inorganic salts on the water solubility of the non-ionic surfactants is similar to that of increasing the temperature; in fact they have greater affinity for water than do the ether linkages in the non-ionic surfactants. Therefore, presence and/or addition of electrolytes to an aqueous solution of a non-ionic surfactant lowers the "cloud point" permitting to separate two phases without increasing too much the temperature.

Generally, the non ionic surfactants which can be usefully employed in the process of this invention have a cloud point of at least 5° C. and preferably between 10° C. and 80° C., more preferably between 15° C. and 70° C. but can be used also surfactants having a cloud point above 80° C. if the antibiotic substances show substantial stability above such temperature.

As for the cationic surfactants, it is clear that the final concentration of the salt in the mixture which provokes the separation in two phases depends not only on the temperature but also on the HLB value of the particular cationic surfactant used. If the cationic surfactant exhibits a high HLB value it is more difficult to separate the two phases and a larger amount of electrolyte has to be added. If the cationic surfactants show a HLB of about 16–17 a lower amount of salt is necessary.

Usually, the electrolytes which are added for favoring the separation in two phases are water soluble salts which do not react with the antibiotic or negatively affects its stability.

Inorganic water soluble salts, e.g. alkali metals and ammonium halides are generally preferred for their low costs and high effectiveness.

The alkali metal salts which can be employed are Li, Na and K salts even if the sodium salts are preferred.

The halide used as counter ion can be chosen between Cl, Br, and I, the chlorine being the preferred one.

The final concentration of the added salt depends also on the saline concentration of the original broth. Under the usual fermentation conditions, the concentration of the added salt in the extraction mixture containing non-ionic surfactants (a) is generally comprised between 10% and 30% (w/v), preferably, about 15–20%. The concentration of the added salt in the extraction mixture containing the cationic surfactant (b) is generally comprised between, 5% and saturated concentration but, preferably, it is preferred to use a concentration around 25–30% (w/v).

The temperature at which it is preferred to carry out the separation step can vary from room temperature to 70° C.

Lowering the concentration of the salts requires higher temperature for phase separation.

During the phase separation step, it is advisable to maintain the pH value lower than 7 in order to avoid possible chemical degradation of the substance.

Following this procedures, it is possible to separate a surfactant phase which is about 10% of the total volume of the original extraction mixture and which contains practically all antibiotic and surfactant and a phase containing less than 5% of antibiotic which can be discarded.

In a preferred embodiment of the invention, use of a polyoxyethylene-tert-octyl-phenyl ester as non-ionic surfactant, the addition of an amount of sodium chloride corresponding to a concentration up to 250 g/l in the total extraction mixture and an increase of the temperature of 20° C.–40° C. gives good results; in this case, it may be useful to prolong the heating for 30–60 minutes to complete the separation.

In a further preferred embodiment of the invention, use of the amido propyl dimethylamine oxide as cationic surfactant, the addition of an amount of sodium chloride corresponding to a concentration up to 20% in the total extraction mixture and an increase of the temperature of 40° C. gives good results; also in this case, it may be useful to prolong the heating for 30–60 minutes.

Practically this step allows to collect a substantial amount of the antibiotic produced by the fermentation process in a relatively small volume liquid phase without requiring laborious extraction and concentration procedures.

The final step comprises the removal of the surfactant layer and the selective separation of the antibiotic from the surfactant by addition of an organic solvent miscible with the surfactant phase and wherein the antibiotic is insoluble, which provokes precipitation of antibiotic.

Among the solvents which are usefully employed for this purpose, both inert organic solvents miscible with water such as acetone, acetonitrile, lower alkanols and organic inert solvents not miscible with water, such as for instance toluene, ethyl acetate, can be used.

The organic aprotic solvents such as acetone, are largely preferred since there are no risks of chemical interactions with the lactone moiety of the antibiotic.

When an organic solvent miscible with water is used in order to obtain a complete separation of antibiotic from the surfactant, it is preferred to use a ratio organic solvent/ surfactant phase of at least 5/1–9/1 v/v. When organic solvents not miscible with water are used, two different phases are formed. The lower phase essentially consists of water (which is discarded) while the upper phase essentially consists of an emulsion formed by organic solvent, water, surfactant and solid antibiotic. Water may be eliminated from said upper phase by azeotropic distillation by continuous addition of the same organic solvent. At the end of the distillation a clear phase is obtained which is concentrated.

The solid which is precipitated is collected by filtration according to known techniques, washed with the same organic solvent and dried under vacuum at 40° C. The antibiotic precipitates with the salt used in the salting step, which represents most of the weight of the crude product.

The separation of the antibiotic from the salts can be easily achieved by well known desalination procedures. Said operation may be carried out by applying ultrafiltration techniques (for instance, by using membranes of the Filmtee Co.) or by pouring the solution containing the antibiotic through a non-ionogenic macroreticular cross-linked resin (for instance, Amberlite XAD-7 or other resins of this type) whereby the glycolipodepsipeptide antibiotic is adsorbed from the aqueous mixture and then eluted with acetone/ water mixture.

The following examples have to be considered merely illustrative and not limitative for the present invention.

EXAMPLE 1

To a stirred solution of antibiotic A/16686 enriched in factor A2 (330 ppm, HPLC extimate) harvest broth (20 l) obtained as described in European Patent Application Publication No. 259780 adjusted at pH 2.6 with $H_2SO_4$ (33%), 600 ml of Triton X-100 are added at 10° C. The mixture was allowed to reach room temperature and after 1 hour, the mixture was filtered on a buchner funnel through a cake of Clarcel Flo-Ma filter aid. The resulting solution had a volume of 17.5 l and about 90% of the initial activity was recovered. The exhausted mycelium was discarded. The filtrate, heated at 40° C., was stirred, while 2.8 kg of sodium chloride were added; then the filtrate was allowed to stand for a night at room temperature to separate in two phases. The heavy phase (16.4 l) was discarded, while the light phase (1.9 l), containing almost all antibiotic A/16686 and Triton X-100, was diluted with 9 l of acetone. The precipitated solid was collected by filtration, washed with 1 l of acetone and dried under vacuum at 40° C. for 4 hours to give 191.3 g of crude antibiotic A/16686 having the following composition:

| HPLC titre (referred to factor A2) | 1.9% |
| Solvent + water | about 10% |
| NaCl | 85–90%. |

HPLC was done with a Hewlett-Packard model 1090 liquid chromatograph connected to a HP 3357 computing system. The chromatographic conditions were:

| column | RP 18 5 micrometer (250*4.6 mm) Brownlee Labs |
| precolumn | RP 18 7 micrometer Brownlee Labs |
| mobile phase A | 0.025 M $NAH_2PO_4$—$CH_3CN$ 80:20 |
| mobile phase B | 0.025 M $NaH_2PO_4$—$CH_3CN$ 20:80 |
| gradient profile | time, min (% B) 0 (27), 5 (27), 30 (95) |
| flow rate | 1.5 ml/min |
| oven temperature | 40° C. |
| injection volume | 10 microliter |
| wavelength | 254 nm |

EXAMPLE 2

To a stirred solution of antibiotic A/16686 enriched in factor A2 (354 ppm, EPLC extimate) harvest broth (4 l) obtained as described in European Patent Application Publication No. 259780 adjusted at pH 2.6 with $H_2SO_4$ (33%), 120 ml of Triton X-100 are added at 10° C. The mixture was allowed to reach room temperature and after 1 hour, the mixture was filtered on a buchner funnel through a cake of Clarcel Flo-Ma filter aid. The filtrate, heated at 40° C., was stirred, while 730 g of sodium chloride were added; then the filtrate was allowed to stand for a night at room temperature to separate in two phases.

The heavy phase (3300 ml) was discarded, while the light phase (430 ml), containing almost all antibiotic A/16686 and Triton X-100, was diluted with 430 ml of toluene.

Two phases were formed: a lower phase (300 ml) and an upper phase (560 ml).

The lower phase containing water was discarded.

The upper organic phase is an emulsion which contains water, toluene, Triton and solid antibiotic. Said organic phase was submitted to azeotropic distillation under reduced pressure by adding toluene (1 l) until the water is eliminated.

A resulting concentrated solution (500 ml) was obtained. The precipitated solid was collected by filtration, washed with 50 ml of toluene and dried under vacuum at 40° C. for 4 hours to give 19.4 g of crude antibiotic A/16686 having a 3.7% b.W. HPLC titre.

EXAMPLE 3

To a stirred solution of antibiotic A/16686 enriched in factor A2 (330 ppm, HPLC extimate) harvest broth (20 l) obtained as described in European Patent Application Publication No. 259780 adjusted at pH 2 with $H_2SO_4$ (33%), 600 ml of Triton® X-114 are added at 4° C. The mixture was stirred at 4° C. for 2 hours. The mixture was then filtered on a buchner funnel through a cake of Clarcel Flo-Ma filter aid. The resulting solution had a volume of 18 l and contained about 85% of the initial activity. The filtrate was heated at 60° C., and kept overnight between 50° C. and 60° C. thus obtaining the separation in two phases. The light phase (16.2 l) was discarded, while the heavy phase (1.8 l), containing almost all antibiotic A/16686 and Triton® X-114, was diluted with 11 l of acetone. The precipitated solid was collected by filtration, washed with acetone and dried under vacuum at 40° C. to give 25 g of crude antibiotic A/16686 having an HPLC assay of 16.9%.

EXAMPLE 4

To a stirred solution of antibiotic A/16686 enriched in factor A2 (354 ppm, HPLC extimate) harvest broth (2 l) obtained as described in European Patent Application Publication No. 259780 adjusted at pH 2.6 with $H_2SO_4$ (33%), 105 ml of hemonyx® CDO (1.6%) are added at 10° C. The mixture was allowed to reach room temperature and after 1 hour, the mixture was filtered on a buchner funnel through a cake of Clarcel Flo-Ma filter aid. The filtrate, heated at 40° C., was stirred, while 540 g of sodium chloride were added; then the filtrate was allowed to stand for a night at room temperature to separate in two phases.

The heavy phase (1.8 l) was discarded, while the light phase (75 ml), containing almost all antibiotic A/16686 and Ammonyx® CDO, was diluted with 500 ml of acetone. The precipitated solid was collected by filtration, washed with acetone and dried under vacuum at 40° C. to give 158 g of crude antibiotic A/16686 having a HPLC titre (referred to factor A2) of 1.36%.

We claim:

1. A process for recovering an antibiotic or a mixture thereof, produced by the fermentation of Actinoplanes sp. ATCC 33076 or an antibiotic producing mutant thereof, from a fermentation broth or a process stream which comprises:

a) adjusting the pH of said broth or said stream to a pH value ranging from 1–3 and the temperature to a range from 0° C. to 30° C.;

b) extracting said broth or said process stream with a cationic surfactant having a hydrophilic-liphophilic balance not higher than 19.4 in which said cationic surfactant is selected from the group consisting of amine oxides and polyoxyethylene amines, and said surfactant is utilized in a sufficient quantity to extract said antibiotic to form an extract;

c) raising the temperature of said extract to a temperature no greater than 30° C. above room temperature, and optionally adding an electrolyte to said extract, in order to cause said extract to separate into two phases, in which one phase is an aqueous phase and the second phase is a surfactant containing organic phase;

d) separating said surfactant containing phase from said aqueous phase;

e) adding an organic solvent to said surfactant containing phase, in a quantity sufficient to cause said antibiotic to precipitate from solution in said surfactant phase to form a precipitated antibiotic, and;

f) collecting said precipitated antibiotic by filtration.

2. A process according to claim 1 in which said electrolyte is a water soluable inorganic salt.

3. A process according to claim 1 in which said organic solvent is selected from the group consisting of acetone acetonitrile, ethanol, toluene, and ethyl acetate.

4. A process for recovering an antibiotic or a mixture thereof, produced by the fermentation of Actinoplanes sp. ATCC 33076 or an antibiotic producing mutant thereof, from a fermentation broth or a process stream which comprises:

a) adjusting the pH of said broth or said stream to a pH value ranging from 1–3 and the temperature to range from 0° C. to 30° C.;

b) extracting said broth or said process stream with a polyoxyethylene non-ionic surfactant having a hydrophiliclipophilic balance of at least 10, and a sufficient quantity of said surfactant is utilized to extract said antibiotic to form an extract;

c) raising the temperature of said extract to a temperature no greater than 30° C. above room temperature, and optionally adding an electrolyte to said extract, in order to cause said extract to separate into two phases, in which one phase is an aqueous phase and the second phase is a surfactant containing organic phase;

d) separating said surfactant containing phase from said aqueous phase;

e) adding an organic solvent to said surfactant containing phase in a quantity sufficient to cause said antibiotic to precipitate from solution in said surfactant phase to form a precipitated antibiotic, and;

f) collecting said precipitated antibiotic by filtration.

5. A process according to claim 4 in which said electrolyte is a water soluble inorganic salt.

6. A process according to claim 4 in which said organic solvent is selected from the group consisting of acetone acetonitrile, ethanol, toluene, and ethyl acetate.

* * * * *